United States Patent
Ueno et al.

(10) Patent No.: US 8,759,567 B2
(45) Date of Patent: Jun. 24, 2014

(54) PROCESS FOR PRODUCING PERFLUORO ORGANIC PEROXIDE

(75) Inventors: Katsuya Ueno, Tokyo (JP); Toshiyuki Tanaka, Tokyo (JP); Mayako Takahashi, Tokyo (JP); Kazuhiko Yamada, Tokyo (JP); Fusaaki Takeo, Tokyo (JP); Shoji Furuta, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/248,732

(22) Filed: Sep. 29, 2011

(65) Prior Publication Data

US 2012/0022286 A1 Jan. 26, 2012

Related U.S. Application Data

(63) Continuation of application No. PCT/JP2010/056341, filed on Apr. 7, 2010.

(30) Foreign Application Priority Data

Apr. 8, 2009 (JP) ................................. 2009-094170

(51) Int. Cl.
- *C07C 331/00* (2006.01)
- *C07C 381/00* (2006.01)
- *C07C 21/18* (2006.01)
- *C07C 17/00* (2006.01)

(52) U.S. Cl.
USPC .......................................... 560/302; 570/126

(58) Field of Classification Search
None
See application file for complete search history.

(56) References Cited

U.S. PATENT DOCUMENTS

| 2,792,423 A | | 5/1957 | Young et al. |
| 4,209,599 A | * | 6/1980 | Brady et al. ..................... 526/64 |
| 8,308,087 B2 | * | 11/2012 | Berbee et al. .................. 239/589 |

FOREIGN PATENT DOCUMENTS

| EP | 1 164 130 A2 | 12/2001 |
| EP | 1 164 130 A3 | 12/2001 |
| JP | 53-44514 | 4/1978 |
| JP | 11-511464 | 10/1999 |
| JP | 2003-155272 | 5/2003 |
| JP | 2006-89472 | 4/2006 |
| JP | 2007-308388 | 11/2007 |
| JP | 2008-44863 | 2/2008 |

OTHER PUBLICATIONS

JP-200689472 Derwent Abstract 2006 pp. 1-2.*
International Search Report issued Jun. 8, 2010 in PCT/JP2010/056341 filed Apr. 7, 2010.
Extended Search Report issued Jan. 2, 2013 in European Patent Application No. 10761728.4-1211.

* cited by examiner

*Primary Examiner* — Clinton Brooks
(74) *Attorney, Agent, or Firm* — Oblon, Spivak, McClelland, Maier & Neustadt, L.L.P.

(57) ABSTRACT

To provide a process for safely producing a perfluoroacyl peroxide with good productivity.

By supplying a perfluoroacyl halide-containing organic solvent solution, an aqueous solution of hydrogen peroxide or a metal peroxide, and an aqueous basic alkali metal compound solution to a tubular reactor to allow them to react with one another, in a flow rate ratio of, as represented by molar ratio of the compounds in the solutions, from 1.00 to 1.35 of the basic alkali metal compound and from 0.60 to 40 of hydrogen peroxide or the metal peroxide per 1 of the perfluoroacyl halide, the yield of a perfluoroacyl peroxide based on the material perfluoroacyl halide can be remarkably improved as compared with conventional technique.

15 Claims, 1 Drawing Sheet

PROCESS FOR PRODUCING PERFLUORO ORGANIC PEROXIDE

This application is a continuation of PCT Application No. PCT/JP2010/056341, filed Apr. 7, 2010, which is based upon and claims the benefit of priority from Japanese Patent Application No. 2009-094170 filed on Apr. 8, 2009. The contents of those applications are incorporated herein by reference in its entirety.

TECHNICAL FIELD

The present invention relates to a process for producing a fluorocarbon acyl peroxide.

BACKGROUND ART

A perfluoroacyl peroxide is usually produced by stirring a hydroxide such as potassium hydroxide or sodium peroxide and hydrogen peroxide (or a metal peroxide such as $Na_2O_2$) together with a halogenated alkyl compound dissolved in an organic solvent. A perfluoroacyl peroxide usually has low thermal stability, and the yield of a peroxide may be decreased due to autolysis by heat of reaction. Further, since a perfluoroacyl peroxide is usually hydrolyzed, a competitive reaction of a reaction of formation of a perfluoroacyl peroxide and a reaction of hydrolysis of the perfluoroacyl peroxide occurs, and as stirring or emulsification becomes intense, the hydrolysis is accelerated and as a result, the recovery rate tends to be decreased.

Patent Document 1 discloses a process for continuously producing a peroxyester by passing an acid chloride, a hydroperoxide and an aqueous alkali metal hydroxide through continuous two reactors with mechanical stirring. The peroxy ester disclosed in Examples of this Patent Document is one containing only carbon, hydrogen and oxygen, and this Patent Document discloses no Example relating to production of a perfluoroacyl peroxide.

Patent Document 2 discloses a process for continuously producing a fluorocarbon acyl peroxide by reaction a hydroxide, a peroxide and an acyl halide with continuous stirring. This Patent Document 2 discloses that the reaction product is vigorously stirred by means of ultrasonic waves, a static mixing device or the like to complete the reaction in a shorter time thereby to obtain a peroxide with good yield. However, Example 13 discloses a process for producing perfluoropropionyl peroxide $[CF_3CF_2(C=O)O]_2$, but the yield is based on starting material $C_2F_5COCl$, and in a system without addition of a surfactant, the yield is from 18 to 23% and is very low. Further, the yield is improved to 43% by addition of a surfactant, but the yield is still low, and in a case where the surfactant is harmful when the product is used, a process to remove the surfactant is required. Further, the use of the surfactant is undesirable since it is a compound $(CF_3CF_2CF_2CF_2CF_2CF_2CF_2COONH_4)$ analogous to PFOA of which bioaccumulation potential is pointed out.

Patent Document 3 disclose a process for producing a fluorocarbon acyl peroxide by the batch by reacting a hydroxide, a peroxide and an acyl halide under batch conditions. This Patent Document 3 discloses a process for producing perfluoropropionyl peroxide $[CF_3CF_2(C=O)O]_2$ in Example 2, and the yield is at a level of 82% based on the starting material $C_2F_5COCl$. Although the reaction time is not disclosed in this Example, there is a problem in productivity since the reaction is carried out by the batch.

Patent Document 4 discloses a continuous process for preparing a perfluoroorganic peroxide by means of a microreactor. By the microreactor, the flow path of the reactor is very narrow, and the reactor volume per unit reactor length is small. Thus, in order to secure a sufficient retention time to complete the reaction, it is necessary to make the flow rate of the reaction liquid to be supplied to the reactor be low, or to make the reactor be long. However, when a large amount of production is required, by the former means, since the amount of production of each reactor is small, a very large number of microreactors are required, and instrumentation devices therefor are also increased. Further, the latter means has a disadvantage such that the pressure loss of the flow path will be significant due to the reactor being long. Accordingly, preparation by means of such microreactors is also problematic for production of a large amount of a perfluoroorganic peroxide.

PRIOR ART DOCUMENTS

Patent Documents

Patent Document 1: JP-A-53-44514
Patent Document 2: JP-A-11-511464
Patent Document 3: U.S. Pat. No. 2,792,423
Patent Document 4: JP-A-2005-244334

DISCLOSURE OF INVENTION

Technical Problem

A process for producing a perfluoroacyl peroxide which is thermally unstable and is likely to undergo autolysis, safely with good productivity, by using a material which is easily handled and is readily available, without using an assistant such as a surfactant, has been required.

Solution to Problem

The present invention provides a process for continuously producing a perfluoroacyl peroxide, which comprises introducing a perfluoroacyl halide-containing organic solvent solution, an aqueous solution of hydrogen peroxide or a metal peroxide and an aqueous solution of a basic alkali metal compound to an inlet of a tubular reactor, mixing the solutions in the tubular reactor to allow them to react with one another, and sending a liquid containing a perfluoroacyl peroxide out from an outlet of the tubular reactor, wherein the perfluoroacyl halide-containing organic solvent solution, the aqueous solution of hydrogen peroxide or a metal peroxide and the aqueous basic alkali metal compound solution are introduced to the tubular reactor in a flow rate ratio of, as represented by molar ratio of the compounds in the solutions, from 1.00 to 1.35 of the basic alkali metal compound and from 0.60 to 40 of hydrogen peroxide or the metal peroxide per 1 of the perfluoroacyl halide.

Advantageous Effects of Invention

By using a perfluoroacyl halide-containing organic solvent solution, an aqueous solution of hydrogen peroxide or a metal peroxide such as $Na_2O_2$ and an aqueous solution of a basic alkali metal compound as preparation materials, and by supplying from 0.60 to 40 mol of hydrogen peroxide or the metal peroxide and from 1.00 to 1.35 mol of the basic alkali metal compound per 1 mol of the perfluoroacyl halide, to a reactor continuously, the yield of a perfluoroacyl peroxide based on the material perfluoroacyl halide can be remarkably improved as compared with conventional technique. Further, in the present invention, since an assistant such as a surfactant is unnecessary, a process for removing such an assistant is unnecessary.

DESCRIPTION OF EMBODIMENTS

Figure 1:
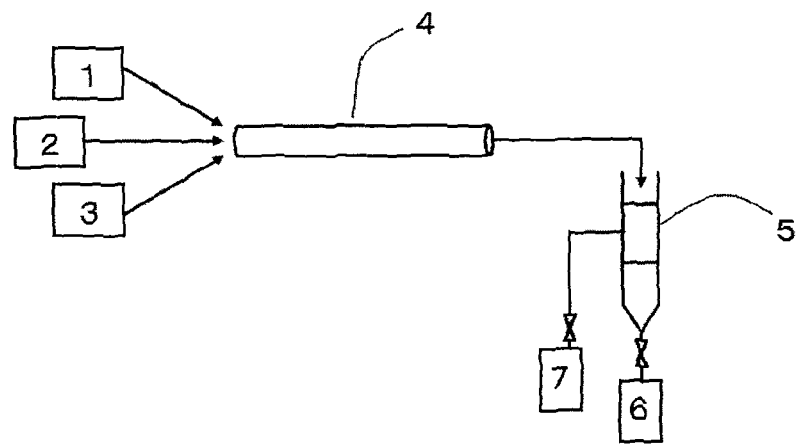
FIG. 1 is a view schematically illustrating a tubular reactor shown in Example 1.

In production of a perfluoroacyl peroxide in the present invention, the perfluoroacyl halide used as an essential material component is preferably a compound represented by the following formula (1):

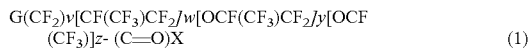

$$G(CF_2)v[CF(CF_3)CF_2]w[OCF(CF_3)CF_2]y[OCF(CF_3)]z-(C=O)X \quad (1)$$

wherein G is a fluorine atom or a pentafluorophenoxy group, X is a halogen atom, v is an integer of from 0 to 10, w is 0 or 1, y is an integer of from 0 to 7, and z is 0 or 1, provided that v+w≥1.

G is preferably a fluorine atom, and X is preferably a fluorine atom or a chlorine atom. v is preferably an integer of from 1 to 5, and y is preferably an integer of from 0 to 2. It is particularly preferred that G is a fluorine atom, X is a fluorine atom or a chlorine atom, v is 2 or 4, and w+y+z is 0.

The perfluoroacyl halide may, for example, be specifically preferably perfluoroethanoyl chloride, perfluoroethanoyl fluoride, perfluoropropanoyl chloride, perfluoropropanoyl fluoride, perfluorobutanoyl chloride, perfluorobutanoyl fluoride, perfluoropentanoyl chloride, perfluoropentanoyl fluoride, perfluorohexanoyl chloride, perfluorohexanoyl fluoride, perfluoro-2,5-dimethyl-3,6-dioxanonanoyl fluoride, perfluoro-2,5,8-trimethyl-3,6,9-tolyoxadodecanoyl fluoride or perfluoro-2-methyl-3-oxahexanoyl fluoride. Preferred is perfluoropropanoyl chloride, perfluoropropanoyl fluoride, perfluorobutanoyl chloride or perfluorobutanoyl fluoride in view of availability and easy preparation, and perfluoropropanoyl chloride is particularly preferred.

Further, the perfluoroacyl peroxide to be prepared by the present invention is preferably $\{R(C=O)O\}_2$ (wherein R is $G(CF_2)v[CF(CF_3)CF_2]w[OCF(CF_3)CF_2]y[OCF(CF_3)]z-$, G is a fluorine atom or a pentafluorophenoxy group, X is a halogen atom, v is an integer of from 0 to 10, w is 0 or 1, y is an integer of from 0 to 7, and z is 0 or 1, provided that v+w≥1.

Further, in the present invention, as the organic solvent, an organic solvent which is nonreactive with a peroxide and in which a perfluoroacyl halide and a perfluoroacyl peroxide are easily soluble, is used. The organic solvent is preferably a fluorinated organic solvent or a hydrocarbon solvent, particularly preferably a fluorinated organic solvent such as a fluorocarbon, a chlorofluorocarbon, a hydrofluorocarbon or a hydrofluoroether. The organic solvent may, for example, be $C_6F_{13}H$, $CF_3CF_2CHCl_2$, $CF_2ClCF_2CHClF$, $C_2F_5I$, $C_4F_9I$, $C_6F_{13}I$, $CF_2ClCFCl_2$, $CF_3CH_2CF_2H$, $CF_3CF_2CH_2CF_2H$, $CHClFCF_2CF_2Cl$, $F(CF_2)_4OCH_3$, $F(CF_2)_2OC_2H_5$, $H(CF_2)_4OCH_3$, $H(CF_2)_4OC_2H_5$, perfluorobutyltetrahydrofuran, perfluoropropyltetrahydrofuran, perfluorohexane, dichloropentafluoropropane, hexane, xylene, benzene, cyclohexane or mineral spirit, or a mixture thereof. With respect to the perfluoroacyl halide-containing organic solvent solution, the concentration of the perfluoroacyl halide in the organic solvent solution is preferably from 1 to 80 mass %, particularly preferably from 3 to 60 mass %. If the concentration exceeds 80 mass %, the risk of autolysis of the product is high, thus leading to difficult handling. If the concentration is less than 1 mass %, the amount of the solvent used is very large, thus leading to low productivity, and such is industrially unfavorable.

In the present invention, as hydrogen peroxide or the metal peroxide, specifically, hydrogen peroxide, sodium peroxide or barium peroxide may, for example, be preferably mentioned. Particularly in view of handling efficiency and economical efficiency, hydrogen peroxide is preferred. In a case where hydrogen peroxide is used, it is preferably used alone, and in a case where another peroxide is used, it may be used alone or as a mixture.

Further, with respect to the aqueous solution of hydrogen peroxide or a metal peroxide, the concentration of hydrogen peroxide or the metal peroxide in the aqueous solution is preferably from 1 to 60 mass %, particularly preferably from 5 to 50 mass %. If the concentration exceeds 60 mass %, the yield of the product will be decreased, and if it is less than 1 mass %, the reaction efficiency will be remarkably decreased, and such is industrially unfavorable.

In the present invention, the basic alkali metal compound is an alkali metal compound of which the aqueous solution shows basicity, and is preferably a hydroxide, a carbonate, a hydrogen carbonate or the like of an alkali metal. Specifically, for example, sodium hydroxide, potassium hydroxide, sodium hydrogencarbonate, potassium hydrogencarbonate, sodium carbonate or potassium carbonate may be preferably mentioned, and among them, potassium hydroxide is particularly preferred. The basic alkali metal compound may be used alone or as a mixture.

Further, with respect to the aqueous solution of a basic alkali metal compound, the concentration of the basic alkali metal compound in the aqueous solution is preferably from 1 to 60 mass %, particularly preferably from 5 to 50 mass %. If the concentration exceeds 60 mass %, the yield of the product will be decreased, and if it is less than 1 mass %, the reaction efficiency will be remarkably decreased, and such is industrially unfavorable.

The process for producing a perfluoroacyl peroxide of the present invention is carried out by a continuous process. Production by a continuous process has such advantages that safe production with high yield is possible even in a case where the reaction to form a product from a material involves heat generation as in the present invention, and also in a case where the product to be obtained is thermally unstable and is decomposed with heat generation, since the amounts of the materials and the product staying in the interior of the reactor is small as compared with production by the batch. Further, it also has advantages such that the amount of production can be increased by continuous production, as compared with a batch type production apparatus having a size at the same level.

The process for producing a perfluoroacyl peroxide of the present invention will be specifically described. FIG. 1 is a view schematically illustrating an embodiment of the present invention. An organic solvent solution 1 of a perfluoroacyl halide, and an aqueous solution 2 of hydrogen peroxide or a metal peroxide and an aqueous solution 3 of a basic alkali metal compound as materials are continuously introduced at a specific flow rate from an inlet of a tubular reactor 4. The tubular reactor 4 has a mixing zone to uniformly mix the respective solutions, and the introduced solutions are mixed in the tubular reactor and the reaction proceeds. Since the organic solvent solution and the aqueous solution are immiscible, the reaction for formation of the perfluoroacyl peroxide proceeds at the interface between the organic solvent solution and the aqueous solution. Thus, it is preferred to more uniformly and finely disperse and mix the organic solvent solution and the aqueous solution. A liquid sent out from an outlet of the tubular reactor is introduced to a two phase separation tank 5. The liquid sent out of the tubular reactor contains the organic solvent solution and the aqueous solution which are immiscible with each other, and is separated into two phases of an organic phase and an aqueous phase in the two phase separation tank 5. After separation into two phases, the organic phase and the aqueous phase are respectively recovered in an organic phase recovery tank 6 and an aqueous phase recovery tank 7. The formed perfluoroacyl peroxide is contained in the organic phase and is recovered from the organic phase recovery tank 6.

In the present invention, the flow of the organic solvent solution 1, the flow of the aqueous solution 2 and the flow of the aqueous solution 3 preferably meet at the inlet of the tubular reactor 4. Otherwise, the flow of the aqueous solution 2 and the flow of the aqueous solution 3 to be introduced to the tubular reactor 4 may preliminarily meet each other, and the resulting flow may be introduced to the tubular reactor 4. Since the organic solvent solution 1 and the aqueous solutions such as the aqueous solution 2 are immiscible with each other, the flow of the organic solvent solution 1 and the flow of the aqueous solutions such as the aqueous solution 2 preferably meet at the inlet of the tubular reactor 4.

The tubular reactor is preferably one having a structure capable of heating/cooling at a jacket and having a structure capable of continuously adding the organic solvent solution and the aqueous solutions uniformly. The installation state of the tubular reactor is not particularly limited, and the tubular reactor may be installed in a vertical direction, in a horizontal direction, in an oblique direction or the like. The cross-sectional shape of a reaction part of the tubular reactor is not particularly limited, and it may, for example, be a circular form, an elliptic form, a semicircular form, a triangular form, a quadrangular form such as a square, a rectangle or a trapezoid, or a polygonal form such as a pentagonal form or a hexagonal form. Preferred is a circular form in view of easiness of preparation.

The tube length of the reaction part of the tubular reactor is preferably from 0.01 to 1,000 m, more preferably from 0.05 to 10 m, particularly preferably from 0.1 to 5 m. If the length of the reactor is too short, the retention time of the reaction mixture tends to be short, and the yield of the perfluoroacyl peroxide will be decreased. If it is too long, the pressure loss between a supply port of the reaction mixture and an output port after the reaction will be significant, and the reaction mixture will not stably flow in the tubular reactor.

The internal cross-sectional area of the tubular reactor is preferably from $1.0 \times 10^{-7}$ to $5.0 \times 10^{-4}$ m$^2$, particularly preferably from $2.0 \times 10^{-7}$ to $1.0 \times 10^{-4}$ m$^2$. The internal cross-sectional area of the tubular reactor is an area of a cross section of a flow path through which the reaction liquid flows, in a direction vertical to the direction of the liquid flow. If the internal cross-sectional area is smaller than $1.0 \times 10^{-7}$ m$^2$, preparation of a continuous reactor will be difficult. In addition, since the reactor volume per unit reactor length tends to be small, the length of the reactor required to complete the reaction tends to be long, whereby the pressure loss of the flow path tends to be significant. If the internal cross-sectional area is larger than $5.0 \times 10^{-4}$ m$^2$, the wall area per unit volume of the reaction part tends to be small, whereby the heat removal efficiency tends to be decreased, thus leading to a decrease in the yield.

In order that the organic solvent solution and the aqueous solutions which are immiscible are uniformly and finely dispersed and mixed, it is preferred to provide a mixing zone in the tubular reactor. This mixing zone is a zone having, for example, a static mixing device, a filling, an ultrasonic mixing device, a mechanical mixing device or the like provided on the flow path in the tubular reactor. The static mixing device may, for example, be a static mixer (Stator-tube mixer type, spiral mixer type). The filling may be a filling having a diameter smaller than the inner diameter of a capillary forming the flow path (for example, resin pellets, Raschig rings, Lessing rings, pall rings, saddles or Sulzer packing). Particularly, it is preferred to provide a static mixing device in the flow path to mix the organic solution and the aqueous solutions which are immiscible with dividing, inverting or converting them.

The flow rate ratio of the perfluoroacyl halide-containing organic solvent solution and the aqueous alkali metal compound solution to be introduced to the tubular reactor is such that the molar ratio of the perfluoroacyl halide to the basic alkali metal compound in the solutions is within a range of perfluoroacyl halide:basic alkali metal compound=1:1.00 to 1.35. The flow rate ratio is more preferably 1:1.02 to 1.30, particularly preferably 1:1.04 to 1.19.

The flow rate ratio of the perfluoroacyl halide-containing organic solvent solution and the aqueous solution of hydrogen peroxide or a metal peroxide to be introduced to the tubular reactor is such that the molar ratio of the perfluoroacyl halide to hydrogen peroxide or the like in the solutions is within a range of perfluoroacyl halide:hydrogen peroxide=1:0.60 to 40. The flow rate ratio is more preferably 1:0.8 to 35, and in view of productivity, it is particularly preferably 1:1 to 10.

In the present invention, a competitive reaction of a reaction of formation of a perfluoroacyl peroxide and a reaction of hydrolysis of the perfluoroacyl peroxide occurs, and from the viewpoint of improvement in the productivity, there is a proper range for the molar ratio of the perfluoroacyl halide to the basic alkali metal compound. If the amount of the basic alkali metal compound is smaller than the above range, the material perfluoroacyl halide tends to remain unreacted, whereby the yield tends to be decreased, and if the amount of the basic alkali metal compound is larger than the above range, the reaction of hydrolysis of the perfluoroacyl peroxide tends to be accelerated, whereby the yield will be decreased. On the other hand, if the amount of hydrogen peroxide or the like is too small, the reaction amount with the perfluoroacyl halide tends to be decreased, and if it is in excess, the productivity tends to be decreased.

The reaction temperature when the above reaction is carried out is preferably within a range of from −30 to +50° C., particularly preferably from −10° C. to 30° C. If the reaction temperature is less than −30° C., the reaction will take long, and if it exceeds +50° C., the reaction of decomposition of the formed perfluoroacyl peroxide will occur, thus leading to a decrease in the yield. Further, the retention time is industrially preferably from 0.1 second to 5 hours.

In the present invention, the liquid sent out of the tubular reactor contains an organic solvent solution and an aqueous solution which are immiscible and is separated into two phases of an organic phase and an aqueous phase, and accordingly by liquid separation, the organic phase and the aqueous phase can respectively be recovered. The yield of the recovered perfluoroacyl peroxide is preferably at least 75%, particularly preferably from 80 to 100%. Further, the organic phase containing the perfluoroacyl peroxide recovered may be subjected to a step of purifying a perfluoroacyl peroxide e.g. by distillation, cleaning or recrystallization. In a case where the purifying step is carried out, the yield of the perfluoroacyl peroxide after purification is decreased by about 20% from the yield at the stage of the organic phase, e.g. by hydrolysis in cleaning or a loss by recovery, and accordingly, the above yield is preferably at least 60%, particularly preferably from 64 to 100%.

In the present invention, the tubular reactor may be used alone, and it is also preferred to use a plurality of tubular reactors in parallel. In a case where a plurality of them are used, it is preferred to use from 2 to 1,000 reactors, more preferably from 2 to 100 reactors. By using a plurality of the reactors, the amount of production of the perfluoroacyl peroxide can properly be controlled.

Now, the present invention will be described in further detail with reference to Examples of the present invention (Examples 1, 4 to 8, 13, 14, 16 to 18, 20 to 24 and 26 to 28) and Comparative Examples (Examples 2, 3, 9 to 12, 15, 19 and 25). However, it should be understood that the present invention is by no means restricted thereto.

EXAMPLES

A liquid obtained by the reaction was subjected to compositional analysis by means of concentration titration and gas chromatography to determine the $C_2F_5COCl$ conversion rate, the $(C_2F_5COO)_2$ selectivity and the $(C_2F_5COO)_2$ yield as follows. The concentration titration was carried out by the following means.

Into an Erlenmeyer flask having an internal capacity of 100 ml, 25 ml of acetic acid and 2 ml of an aqueous saturated potassium iodide solution are put in this order, and about 0.2 g of a sample is accurately weighed and added. The flask is airtightly sealed and the content is mixed, followed by reaction at dark place for 10 minutes. Titration is carried out with a 0.025 mol/L sodium thiosulfate aqueous solution until the color of iodine disappears. The same operation is carried out under conditions where no sample is added (blank measurement). The weight percentage of a formed product contained in the sample was calculated in accordance with the following formula 1.

$$\text{wt \%} = \{(V-Vb) \times Mw\}/(800 \times Sa) \quad [\text{Formula 1}]$$

V: Volume (ml) of the 0.025 mol/L sodium thiosulfate aqueous solution required for titration of the sample Vb: Volume (ml) of the 0.025 mol/L sodium thiosulfate aqueous solution required for blank measurement Mw: Molecular weight 326 of the formed product Sa: Weight (g) of the sample $(C_2F_5COCl)$ conversion rate From the results of the compositional analysis, the $(C_2F_5COCl)$ conversion rate was determined in accordance with the following formula.

$(C_2F_5COCl)$ conversion rate (%) = {1-($C_2F_5COCl$ concentration (g/g) at the outlet of the reactor)/($C_2F_5COCl$ concentration (g/g) at the inlet of the reactor)}×100

$(C_2F_5COO)_2$ selectivity

From the results of the compositional analysis, the $(C_2F_5COO)_2$ selectivity was determined in accordance with the following formula.

$(C_2F_5COO)_2$ selectivity (%) = {amount (mol) of $(C_2F_5COO)_2$ formed×2/amount (mol) of consumption of $C_2F_5COCl$}×100

$(C_2F_5COO)_2$ yield

The $(C_2F_5COO)_2$ yield was determined in accordance with the following formula.

$(C_2F_5COO)_2$ yield (%) = ($C_2F_5COCl$ conversion rate)× (($C_2F_5COO)_2$ selectivity))

$(C_2F_5COO)_2$ yield after purification

The $(C_2F_5COO)_2$ yield after purification was determined in accordance with the following formula.

$(C_2F_5COO)_2$ yield (%) after purification = {($C_2F_5COO)_2$ formation rate (mol/hr)×2×reaction time (hr)}/{$C_2F_5COCl$ supply rate (mol/hr)×reaction time (hr)}×100

Example 1

As materials, a $CClF_2CF_2CHClF$ solution (reference symbol 1 in FIG. 1) of perfluoroacyl halide $C_2F_5COCl$, an aqueous hydrogen peroxide solution (reference symbol 2 in FIG. 1) and a KOH aqueous solution (reference symbol 3 in FIG. 1) were used. As the tubular reactor (reference symbol 4 in FIG. 1), a resin tube of which the periphery was covered with a jacket was used. This resin tube has a static mixing device (disposable mixer manufactured by NORITAKE CO., LIMITED, model DSP-MXA3-17) in its interior, and had an inner diameter of 0.003 m and a length of 1.2 m. One tubular reactor was used. The jacket temperature was from 0 to 5° C. $C_2F_5COCl$ was used as a 50 mass % solution of $CClF_2CF_2CHClF$, and its flow rate was 16 g/min. The concentration of the aqueous hydrogen peroxide solution was 35 mass %, the concentration of the KOH aqueous solution was 15 mass %, and these solutions were supplied in a molar ratio of 1.02 based on $C_2F_5COCl$. By supplying these materials to the above-described tubular reactor, reaction was carried out. A liquid obtained at an outlet of the tubular reactor was separated into two phases of an organic phase comprising $CClF_2CF_2CHClF$ as a solvent and an aqueous phase (reference symbol 5 in FIG. 1), and the organic phase was recovered to obtain a $CClF_2CF_2CHClF$ solution (reference symbol 6 in FIG. 1) of $(C_2F_5COO)_2$. The aqueous phase was thrown away (reference symbol 7 in FIG. 1).

The $C_2F_5COCl$ conversion rate was 90%, the $(C_2F_5COO)_2$ selectivity was 91%, and the $(C_2F_5COO)_2$ yield was 82%.

Example 2 to 11

The same operation as in Example 1 was carried out except that hydrogen peroxide and KOH were respectively supplied in a molar ratio of from 0.89 to 1.71 based on $C_2F_5COCl$. The molar ratio and the conversion rate, the selectivity and the yield are shown in Table 1.

Examples 12 to 14

The same operation as in Example 1 was carried out except that KOH was supplied in a molar ratio of 1.05 based on $C_2F_5COCl$ and hydrogen peroxide was supplied in a molar ratio of 0.57, 1.13 or 10.02 based on $C_2F_5COCl$. The molar ratio, and the conversion rate, the selectivity and the yield are shown in Table 1.

Examples 15 to 18

The same operation as in Example 1 was carried out except that KOH was supplied in a molar ratio of 1.13 based on $C_2F_5COCl$ and hydrogen peroxide was supplied in a molar ratio of 0.57, 1.71, 10.02 or 32.79 based on $C_2F_5COCl$. The molar ratio, and the conversion rate, the selectivity and the yield are shown in Table 1.

Examples 19 to 21

The same operation as in Example 1 was carried out except that KOH was supplied in a molar ratio of 1.20 based on $C_2F_5COCl$ and hydrogen peroxide was supplied in a molar ratio of 0.57, 1.13 or 10.02 based on $C_2F_5COCl$. The molar ratio, and the conversion rate, the selectivity and the yield are shown in Table 1.

Example 22

The operation as in Example 1 was carried out except that $C_2F_5COCl$ was used as a 37 mass % solution of $CClF_2CF_2CHClF$, its flow rate was 20 g/min, and hydrogen peroxide and KOH were respectively supplied in a molar ratio of 1.20 based on $C_2F_5COCl$. The $C_2F_5COCl$ conversion rate was 100%, the $(C_2F_5COO)_2$ selectivity was 85% and the $(C_2F_5COO)_2$ yield was 85%.

Example 23

The same operation as in Example 1 was carried out except that in the interior of the resin tube of the tubular reactor, resin pellets (PFA pellets manufactured by FLON INDUSTRY, diameter: 2.0 mm) were used instead of the static mixing device (disposable mixer manufactured by NORITAKE CO., LIMITED, model DSP-MXA3-17). The $C_2F_5COCl$ conversion rate was 96%, the $(C_2F_5COO)_2$ selectivity was 90% and the $(C_2F_5COO)_2$ yield was 87%.

Example 24

Figure 2:
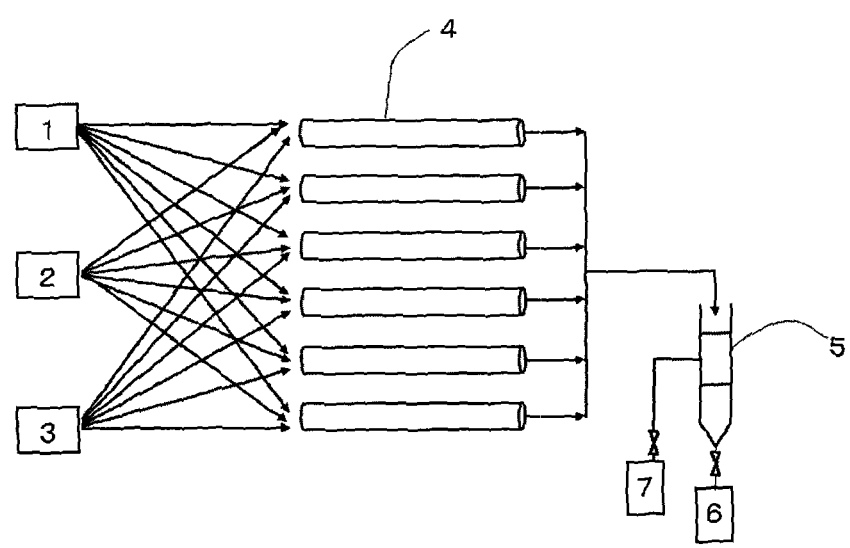
FIG. 2 is a view schematically illustrating a tubular reactor shown in Example 24.

This Example is schematically shown in FIG. 2.

The number of tubular reactors was 6 (reference symbol 4 in FIG. 2). $C_2F_5COCl$ was used as a 44 mass % solution of $CClF_2CF_2CHClF$, and its flow rate was 60 g/min. The $CClF_2CF_2CHClF$ solution of $C_2F_5COCl$, the aqueous hydrogen peroxide solution and the KOH aqueous solution were respectively supplied to the six reactors in parallel. The same operation as in Example 1 was carried out except for the above. The $C_2F_5COCl$ conversion rate was 91%, the $(C_2F_5COO)_2$ selectivity was 86%, and the $(C_2F_5COO)_2$ yield was 79%.

Example 25

The same operation as in Example 1 was carried out except that KOH was supplied in a molar ratio of 2.00 and hydrogen peroxide was supplied in a molar ratio of 1.00 based on $C_2F_5COCl$. The $C_2F_5COCl$ conversion rate was 98%, the $(C_2F_5COO)_2$ selectivity was 14%, and the $(C_2F_5COO)_2$ yield was 13%.

TABLE 1

| | Molar ratio of hydrogen peroxide/ KOH based on $C_2F_5COCl$ | $C_2F_5COCl$ conversion rate (%) | $(C_2F_5COO)_2$ selectivity (%) | $(C_2F_5COO)_2$ yield (%) |
|---|---|---|---|---|
| Ex. 1 (Example of the present invention) | 1.02/1.02 | 90 | 91 | 82 |
| Ex. 2 (Comparative Example) | 0.89/0.89 | 83 | 75 | 62 |
| Ex. 3 (Comparative Example) | 0.98/0.98 | 87 | 82 | 72 |
| Ex. 4 (Example of the present invention) | 1.04/1.04 | 94 | 91 | 85 |
| Ex. 5 (Example of the present invention) | 1.09/1.09 | 100 | 87 | 87 |
| Ex. 6 (Example of the present invention) | 1.13/1.13 | 95 | 86 | 82 |
| Ex. 7 (Example of the present invention) | 1.19/1.19 | 100 | 85 | 85 |
| Ex. 8 (Example of the present invention) | 1.21/1.21 | 100 | 78 | 78 |
| Ex. 9 (Comparative Example) | 1.40/1.40 | 100 | 54 | 54 |
| Ex. 10 (Comparative Example) | 1.50/1.50 | 100 | 46 | 46 |
| Ex. 11 Comparative Example) | 1.71/1.71 | 100 | 26 | 26 |
| Ex. 12 (Comparative Example) | 0.57/1.05 | 94 | 73 | 68 |
| Ex. 13 (Example of the present invention) | 1.13/1.05 | 97 | 79 | 77 |
| Ex. 14 (Example of the present invention) | 10.02/1.05 | 98 | 85 | 83 |
| Ex. 15 (Comparative Example) | 0.57/1.13 | 87 | 82 | 71 |
| Ex. 16 (Example of the present invention) | 1.71/1.13 | 97 | 90 | 87 |
| Ex. 17 (Example of the present invention) | 10.02/1.13 | 100 | 89 | 89 |
| Ex. 18 (Example of the present invention) | 32.79/1.13 | 100 | 84 | 83 |
| Ex. 19 (Comparative Example) | 0.57/1.20 | 97 | 69 | 67 |
| Ex. 20 (Example of the present invention) | 1.13/1.20 | 99 | 78 | 77 |
| Ex. 21 (Example of the present invention) | 10.02/1.20 | 100 | 76 | 76 |
| Ex. 22 (Example of the present invention) | 1.20/1.20 | 100 | 85 | 85 |

TABLE 1-continued

| | Molar ratio of hydrogen peroxide/ KOH based on $C_2F_5COCl$ | $C_2F_5COCl$ conversion rate (%) | $(C_2F_5COO)_2$ selectivity (%) | $(C_2F_5COO)_2$ yield (%) |
|---|---|---|---|---|
| Ex. 23 (Example of the present invention) | 1.20/1.20 | 96 | 90 | 87 |
| Ex. 24 (Example of the present invention) | 1.02/1.02 | 91 | 86 | 79 |
| Ex. 25 (Comparative Example) | 1.00/2.00 | 98 | 14 | 13 |

Purification Step

Example 26

The organic phase obtained in Example 6 was washed with water and left at rest, whereby it was separated into two phases of an organic phase comprising $CClF_2CF_2CHClF$ as a solvent and an aqueous phase, and the organic phase was recovered, whereupon the $(C_2F_5COO)_2$ yield after purification was 64%.

Example 27

A tubular reactor having an inner diameter of 0.003 m and a length of 2.4 m was used, and the number of the tubular reactor was 1. The jacket temperature was from 0 to 5° C. $C_2F_5COCl$ was used as a 44 mass % solution of $CClF_2CF_2CHClF$, and its flow rate was 17.6 g/min. The concentration of the aqueous hydrogen peroxide solution was 35 mass %, and the concentration of the KOH aqueous solution was 15 mass %, and they were respectively supplied in a molar ratio of 1.13 based on $C_2F_5COCl$. Reaction was carried out by supplying these materials to the above-described tubular reactor. A liquid obtained at an outlet of the tubular reactor was separated into two phases of an organic phase comprising $CClF_2CF_2CHClF$ as a solvent and an aqueous phase, and the organic phase was recovered.

The recovered organic phase was washed with water and left at rest, whereby it was separated into two phases of an organic phase comprising $CClF_2CF_2CHClF$ as a solvent and an aqueous phase, and the organic phase was recovered, whereupon the $(C_2F_5COO)_2$ yield after purification was 65%.

Example 28

A tubular reactor having an inner diameter of 0.003 m and a length of 1.2 m was used, and the number of the tubular reactor was 1. The jacket temperature was 7° C. $C_2F_5COCl$ was used as a 44 mass % solution of $CClF_2CF_2CHClF$, and its flow rate was 10 g/min. The concentration of the aqueous hydrogen peroxide solution was 35 mass %, and the concentration of the KOH aqueous solution was 15 mass %, and they were respectively supplied in a molar ratio of 1.13 based on $C_2F_5COCl$. Reaction was carried out by supplying these materials to the above-described tubular reactor. A liquid obtained at an outlet of the tubular reactor was separated into two phases of an organic phase comprising $CClF_2CF_2CHClF$ as a solvent and an aqueous phase, and the organic phase was recovered.

The recovered organic phase was washed with water and left at rest, whereby it was separated into two phases of an organic phase comprising $CClF_2CF_2CHClF$ as a solvent and an aqueous phase, and the organic phase was recovered, whereupon the $(C_2F_5COO)_2$ yield after purification was 64%.

INDUSTRIAL APPLICABILITY

As described above, according to the present invention, a perfluoroacyl peroxide can be produced with a high yield safely and economically. The perfluoroacyl peroxide is one of radical initiators industrially useful in radical reaction of a polyolefin, particularly a fluoroolefin such as tetrafluoroethylene.

REFERENCE SYMBOLS

1: Perfluoroacyl halide-containing organic solvent solution
2: Aqueous hydrogen peroxide solution
3: Aqueous basic alkali metal compound solution
4: Tubular reactor equipped with jacket and static mixing device
5: Two phase separation tank
6: Organic phase recovery tank
7: Aqueous phase recovery tank

What is claimed is:

1. A process for continuously producing a perfluoroacyl peroxide, which comprises introducing a perfluoroacyl halide-containing organic solvent solution, an aqueous solution of hydrogen peroxide or a metal peroxide and an aqueous solution of a basic alkali metal compound to an inlet of a tubular reactor, mixing the solutions in the tubular reactor to allow them to react with one another, and sending a liquid containing a perfluoroacyl peroxide out from an outlet of the tubular reactor, wherein the perfluoroacyl halide-containing organic solvent solution, the aqueous solution of hydrogen peroxide or a metal peroxide and the aqueous solution of a basic alkali metal compound are introduced to the tubular reactor in a flow rate ratio of, as represented by molar ratio of the compounds in the solutions, from 1.00 to 1.35 of the basic alkali metal compound and from 1 to 10 of hydrogen peroxide or the metal peroxide per 1 of the perfluoroacyl halide, wherein the perfluoroacyl halide is $C_2F_5(CO)Cl$.

2. The production process according to claim 1, wherein the aqueous solution of hydrogen peroxide or a metal peroxide is an aqueous hydrogen peroxide solution.

3. The production process according to claim 1, wherein the aqueous solution of a basic alkali metal compound is an aqueous potassium hydroxide solution.

4. The production process according to claim 1, wherein the internal cross sectional area of the tubular reactor is from $1.0 \times 10^{-7}$ to $5.0 \times 10^{-4}$ m².

5. The production process according to claim 1, wherein the tubular reactor has a static mixing device in its interior reaction zone.

6. The production process according to claim 1, wherein the reaction temperature is from −10° C. to 30° C.

7. The production process according to claim 1, wherein the concentration of the perfluoroacyl halide in the perfluoroacyl halide-containing organic solvent solution is from 3 to 60 mass %.

8. The production process according to claim 1, wherein the concentration of hydrogen peroxide or the metal peroxide in the aqueous solution of hydrogen peroxide or a metal peroxide is from 5 to 50 mass %.

9. The production process according to claim 1, wherein the concentration of the basic alkali metal compound in the aqueous solution of a basic alkali metal compound is from 5 to 50 mass %.

10. The production process according to claim 1, wherein the tube length of a reaction part of the tubular reactor is from 0.05 to 10 m.

11. The production process according to claim 1, wherein the organic solvent is a fluorinated organic solvent.

12. The production process according to claim 1, wherein the flow rate ratio is 1.02 to 1.30 of the basic alkali metal compound per 1 of the perfluoroacyl halide.

13. The production process according to claim 1, wherein the flow rate ratio is 1.04 to 1.19 of the basic alkali metal compound per 1 of the perfluoroacyl halide.

14. The production process according to claim 1, wherein the perfluoroacyl peroxide is obtained in a yield of at least 75%.

15. The production process according to claim 14, wherein the yield is from 80 to 100%.

* * * * *